(12) United States Patent
Bruce et al.

(10) Patent No.: US 9,417,185 B1
(45) Date of Patent: Aug. 16, 2016

(54) CONTROLLING LIGHT ARRAYS TO DETERMINE PROPERTIES OF AN OBJECT

(71) Applicant: Google Inc., Mountain View, CA (US)

(72) Inventors: James R. Bruce, Sunnyvale, CA (US); Ryan Hickman, Mountain View, CA (US); James J. Kuffner, Jr., Mountain View, CA (US); Arshan Poursohi, Berkeley, CA (US)

(73) Assignee: Google Inc., Mountain View, CA (US)

( * ) Notice: Subject to any disclaimer, the term of this patent is extended or adjusted under 35 U.S.C. 154(b) by 323 days.

(21) Appl. No.: 14/058,949

(22) Filed: Oct. 21, 2013

Related U.S. Application Data

(60) Provisional application No. 61/716,598, filed on Oct. 21, 2012.

(51) Int. Cl.
| | |
|---|---|
| *G01N 21/55* | (2014.01) |
| *G06T 15/04* | (2011.01) |
| *G06T 15/00* | (2011.01) |
| *G06T 7/40* | (2006.01) |

(52) U.S. Cl.
CPC ........ *G01N 21/55* (2013.01); *G06T 7/40* (2013.01); *G06T 15/00* (2013.01); *G06T 15/04* (2013.01)

(58) Field of Classification Search
None
See application file for complete search history.

(56) References Cited

U.S. PATENT DOCUMENTS

| | | | | |
|---|---|---|---|---|
| 6,839,088 B2* | 1/2005 | Dicarlo | ........... | G01N 21/55 348/223.1 |
| 8,009,192 B2* | 8/2011 | Raskar | ........... | G01J 1/42 235/492 |
| 8,134,555 B2* | 3/2012 | Debevec | ........... | G01B 11/25 345/419 |
| 8,264,490 B2* | 9/2012 | Debevec | ........... | G06K 9/00221 345/419 |
| 8,284,279 B2* | 10/2012 | Park | ........... | G06K 9/2018 348/210.99 |
| 8,300,234 B2* | 10/2012 | Debevec | ........... | G01N 21/55 356/600 |
| 8,462,357 B2* | 6/2013 | Rodrigue | ........... | G01B 11/245 356/601 |
| 8,845,107 B1* | 9/2014 | Coley | ........... | G06T 19/20 345/418 |
| 8,848,201 B1* | 9/2014 | Bruce | ........... | G01B 21/047 356/601 |
| 8,953,037 B2* | 2/2015 | Wang | ........... | G01N 21/55 348/142 |

(Continued)

OTHER PUBLICATIONS

Dana, K. J. et al., 1999, Reflectance and texture of real-world surfaces. ACM Trans. Graph. 18, 1 (Jan.), pp. 1-34.*

(Continued)

*Primary Examiner* — Gordon J Stock, Jr.
(74) *Attorney, Agent, or Firm* — McDonnell Boehnen Hulbert & Berghoff LLP

(57) ABSTRACT

Methods and systems for controlling light arrays to determine properties of an object are described. An example method includes causing illumination of a surface of an object from multiple illumination positions using a programmable array of lights, and receiving images from an image-capture device while the surface of the object is illuminated. For example, the programmable array of lights may be modulated to cause illumination of a portion of the surface of the object from first and second illumination positions, and a first and second image of the surface of the object captured during illumination from the first and second illumination positions respectively may be received. Subsequently, a processor may determine material information for the object based on an amount of specular reflectivity for the surface of the object and reference to a database of known amounts of specular reflectivity for a plurality of materials.

20 Claims, 7 Drawing Sheets

(56) References Cited

U.S. PATENT DOCUMENTS

| | | | | |
|---|---|---|---|---|
| 2003/0231174 | A1* | 12/2003 | Matusik | G06T 9/001 |
| | | | | 345/419 |
| 2005/0068537 | A1* | 3/2005 | Han | G01N 21/4795 |
| | | | | 356/446 |
| 2006/0028474 | A1* | 2/2006 | Pfister | G06T 15/50 |
| | | | | 345/473 |
| 2006/0245632 | A1* | 11/2006 | Nisper | G01J 3/02 |
| | | | | 382/135 |
| 2012/0176478 | A1 | 7/2012 | Wang et al. | |
| 2012/0177283 | A1 | 7/2012 | Wang et al. | |
| 2014/0268160 | A1* | 9/2014 | Debevec | G01N 21/55 |
| | | | | 356/445 |
| 2015/0016711 | A1* | 1/2015 | Tin | G06T 7/0004 |
| | | | | 382/152 |
| 2015/0029310 | A1* | 1/2015 | Tien | H04N 13/0253 |
| | | | | 348/46 |

OTHER PUBLICATIONS

Dong, Y. et al., 2010, Manifold bootstrapping for SVBRDF capture, ACM Trans. Graph. 29 (Jul.), 98:1-98:10.*

Hawkins, T. et al., 2005, A dual light stage, Proc. Eurographics Symposium on Rendering, pp. 91-98.*

Holroyd, M. et al., 2010, A coaxial optical scanner for synchronous acquisition of 3d geometry and surface reflectance. ACM Trans. Graph. 29, 4 (Jul.), 99:1-99:12.*

Margarita Osadchy et al., "Using Specularities for Recognition", International Conference on Computer Vision, p. 1512-1519, 2003.

Wynn, Chris, "An Introduction to BRDF-Based Lighting", NVIDIA Corporation, available at www.nvidia.com/object/BRDFbased_Lighting.html, last updated Oct. 31, 2000.

* cited by examiner

CONTROLLING LIGHT ARRAYS TO DETERMINE PROPERTIES OF AN OBJECT

CROSS-REFERENCE TO RELATED APPLICATIONS

This application claims the benefit of U.S. Provisional Application No. 61/716,598 filed on Oct. 21, 2012, the entirety of which is herein incorporated by reference.

BACKGROUND

In computer graphics, three-dimensional (3D) modeling involves generation of a representation of a 3D surface of an object. The representation may be referred to as a 3D object data model, and can be rendered or displayed as a two-dimensional image via 3D rendering or displayed as a three-dimensional image. 3D object data models may represent a 3D object conceptually using a collection of points in 3D space, connected by various geometric entities such as triangles, lines, curved surfaces, etc. Various techniques exist for generating 3D object data models utilizing point clouds and geometric shapes, for examples.

Being a collection of data, 3D models can be created by hand, algorithmically, or based on data from objects that are scanned, for example. As an example, an artist may manually generate a 3D image of an object that can be used as the 3D model. As another example, a given object may be scanned from a number of different angles, and the scanned images can be combined to generate the 3D image of the object. As still another example, an image of an object may be used to generate a point cloud that can be algorithmically processed to generate the 3D image.

3D object data models may include solid models that define a volume of the object, or may include shell or boundary models that represent a surface (e.g. the boundary) of the object. Because an appearance of an object depends largely on an exterior of the object, boundary representations are common in computer graphics.

SUMMARY

In one example aspect, a method is provided that comprises causing illumination of a first portion of a surface of an object from a first illumination position using a programmable array of lights, and receiving from an image-capture device a first image of the surface of the object. The first image may be captured during illumination of the first portion of the object. The method may also include modulating the programmable array of lights to cause illumination of a second portion of the surface of the object from a second illumination position, and receiving from the image-capture device a second image of the surface of the object. The second image may be captured during illumination of the second portion of the surface of the object. According to the method, a processor may determine material information for the surface of the object based on an amount of specular reflectivity for the surface of the object, with reference to one or more of the first image and the second image, and reference to a database of known amounts of specular reflectivity for a plurality of types of materials.

In another example aspect, a non-transitory computer-readable memory having stored thereon instructions executable by a computing device to cause the computing device to perform functions is provided. The functions may comprise causing illumination of a first portion of a surface of an object from a first illumination position using a programmable array of lights. The functions may also include receiving from an image-capture device a first image of the surface of the object captured during illumination of the first portion of the surface of the object. The functions may also include modulating the programmable array of lights to cause illumination of a second portion of the surface of the object from a second illumination position, and receiving from the image-capture device a second image of the surface of the object captured during illumination of the second portion of the surface of the object. According to the functions, material information for the surface of the object may be determined based on an amount of specular reflectivity for the surface of the object, with reference to one or more of the first image and the second image, and reference to a database of known amounts of specular reflectivity for a plurality of types of materials.

In still another example aspect, a system is provided that comprises a light array, one or more imaging components, a database, and a processor. The light array may be configurable to illuminate a surface of an object from multiple illumination positions. The one or more imaging components may be configured to obtain images of the object while the surface of the object is illuminated. Additionally, the database may include known material information for a plurality of types of materials. The processor may be configured to determine an amount of specular reflectivity for a portion of the surface of the object based on the obtained images, and determine material information for the surface of the object based on the amount of specular reflectivity and reference to the database of known material information.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION

Figure 1:
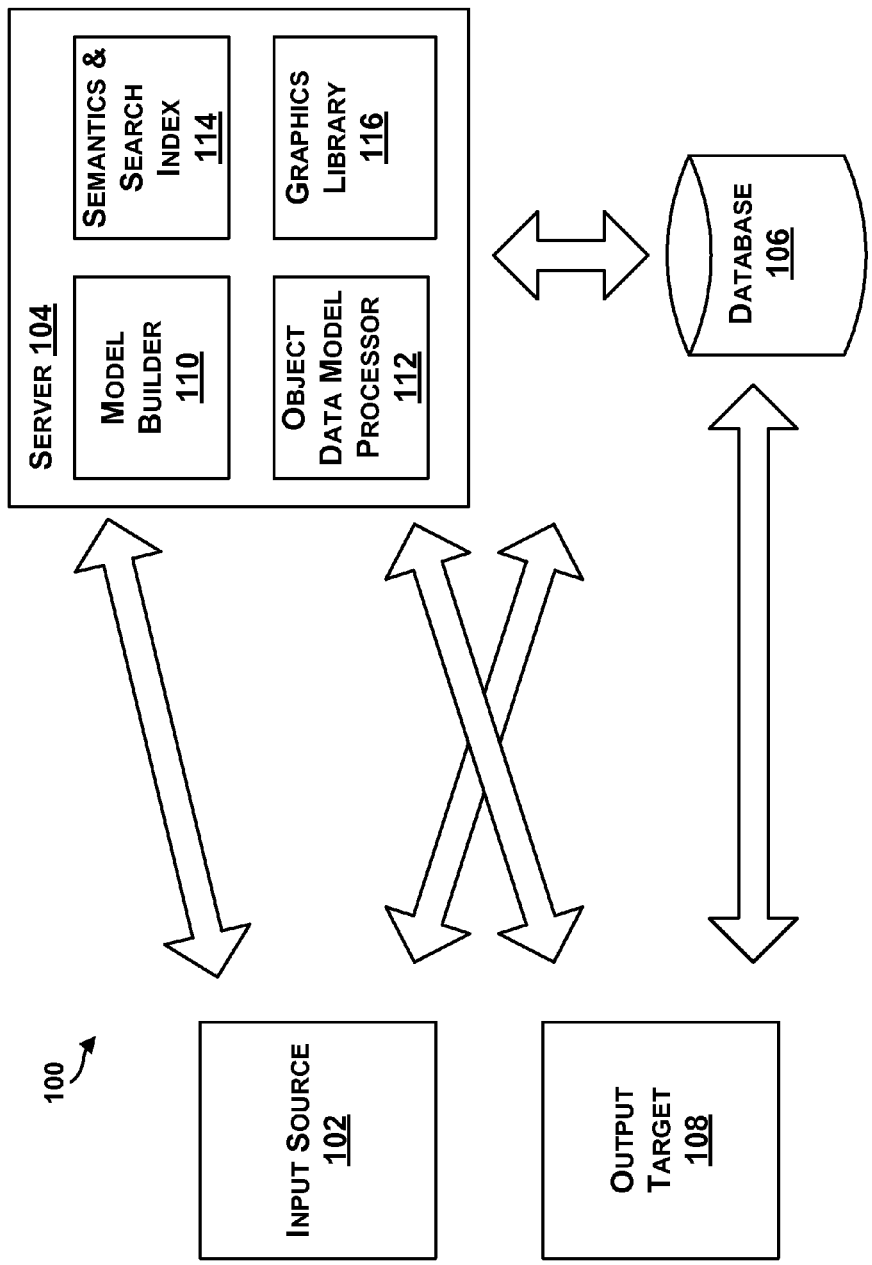
FIG. 1 illustrates an example system for object data modeling.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

This disclosure may disclose, inter alia, methods and systems for controlling light arrays to determine properties of an object. In some examples, an object may be illuminated from a given direction while an image-capture device obtains an image of a surface of the object. Based on information associated with how the object is being illuminated and changes in appearance of the object for images captured for different illumination directions, a processor may determine surface reflectance, geometric, and/or material properties for the surface of the object.

In some instances, surface reflectance properties may be determined by controlling a direction from which a surface of the object is illuminated and monitoring a viewpoint position from which a corresponding image is obtained. As an example, information from one or more images of an object may be referenced to a database of known materials with associated surface reflectance and material properties to differentiate among materials for surfaces of the object. An amount of specular reflectivity or specular highlights may be identified for an image to determine surface reflectance properties for portions of an object. The amount of specular reflectivity may subsequently be referenced to the database to classify one or more portions of the object as a given type of material.

Depending on the type of material of a given portion of the object, the amount of specular reflectivity may vary. Consequently, different types of materials may have different specular reflectivity signatures. The database of known materials with associated surface reflectance properties may therefore be used to determine a type of material corresponding to a particular amount of specular reflectivity. More generally, the database of known materials with associated reflectance properties may be used to determine a type of material corresponding to a particular specular reflectivity signature. A bidirectional reflection distribution function (BRDF) is one example of a specular reflectivity signature. In some examples, a BRDF for an object may be determined using a video stream or images from a high-speed camera. Based on the BRDF and reference to the database of known materials, one or more portions of the object may be classified as a given type of material.

In some instances, a programmable array of lights may be modulated to cause illumination of the object from various illumination positions and with various illumination intensities while multiple images of the object are obtained using one or more cameras. For example, arrays of light-emitting diodes from one or more modular panels may be controlled to provide illumination from a variety of angles. Alternatively, a strip of lights around an object may be used to provide illumination from unique angles by adjusting a position of the strip or modulating one or more lights of the strip.

In another example, a shape of an object or geometric properties of the object may be determined based on multiple silhouette images of an object. For instance, silhouette information for an object may be determined for multiple sides of the object by positioning a camera opposite a direction of illumination. The silhouette information may be combined to approximate a shape for the object.

Referring now to the figures, FIG. 1 illustrates an example system 100 for object data modeling. The system 100 includes an input source 102 coupled to a server 104 and a database 106. The server 104 is also shown coupled to the database 106 and an output target 108. The system 100 may include more or fewer components, and each of the input source 102, the server 104, the database 106, and the output target 108 may comprise multiple elements as well, or each of the input source 102, the server 104, the database 106, and the output target 108 may be interconnected. Thus, one or more of the described functions of the system 100 may be divided up into additional functional or physical components, or combined into fewer functional or physical components. In some further examples, additional functional and/or physical components may be added to the examples illustrated by FIG. 1.

Components of the system 100 may be coupled to or configured to be capable of communicating via a network (not shown), such as a local area network (LAN), wide area network (WAN), wireless network (Wi-Fi), or Internet, for example. In addition, any of the components of the system 100 may be coupled to each other using wired or wireless communications. For example, communication links between the input source 102 and the server 104 may include wired connections, such as a serial or parallel bus, or wireless links, such as Bluetooth, IEEE 802.11 (IEEE 802.11 may refer to IEEE 802.11-2007, IEEE 802.11n-2009, or any other IEEE 802.11 revision), or other wireless based communication links.

The input source 102 may be any source from which a 3D object data model, or 3D model, may be received. In some examples, 3D model acquisition (shape and appearance) may be achieved by working with venders or manufacturers to scan objects in 3D. For instance, structured light scanners may capture images of an object and a shape of the object may be recovered using monochrome stereo cameras and a pattern projector. In other examples, a high-resolution DSLR camera may be used to capture images for color texture information. In still other examples, a raw computer-aided drafting (CAD) set of drawings may be received for each object. Thus, the input source 102 may provide a 3D object data model, in various forms, to the server 104. As one example, multiple scans of an object may be processed into a merged mesh and assets data model, and provided to the server 104 in that form.

The server 104 includes a model builder 110, an object data model processor 112, a semantics and search index 114, and a graphics library 116. Any of the components of the server 104 may be coupled to each other. In addition, any components of the server 104 may alternatively be a separate component coupled to the server 104. The server 104 may further include a processor and memory including instructions executable by the processor to perform functions of the components of the server 104, for example.

The model builder 110 receives the mesh data set for each object from the input source 102, which may include a data set defining a dense surface mesh geometry, and may generate an animated model of the object in 3D. For example, the model builder 110 may perform coherent texture unwrapping from the mesh surface, and determine textures of surfaces emulated from the geometry.

The object data model processor 112 may also receive the mesh data set for each object from the input source 102 and generate display meshes. For instance, the scanned mesh images may be decimated (e.g., from 5 million to 120,000 surfaces) utilizing texture-preserving decimation. Texture map generation can also be performed to determine color texture for map rendering. Texture map generation may include using the mesh data sets (H) that have colors but no UV unwrapping to generate a mesh (D) with UV unwrapping but no colors. UV unwrapping refers to the unwrapping of a 3D mesh to a 2D space for texturing purposes, where the 2D space is denoted, by convention, with "u" and "v" coordinates since "x", "y", and "z" are used for 3D space. As an example, for a single output texture pixel of an image processing may include, for a given point in UV determine a triangle in the mesh's UV mapping (D), and using triangle-local coordinates, move to an associated 3D point on the mesh. A bidirectional ray may be cast along the triangle's normal to intersect with the mesh (H), and color, normal and displacement may be used for an output. To generate an entire texture image, each pixel in the image can be processed.

The semantics and search index 114 may receive captured images or processed images that have been decimated and compressed, and may perform texture resampling and also shape-based indexing. For example, for each object, the semantics and search index 114 may index or label components of the images (e.g., per pixel) as having a certain texture, color, shape, geometry, attribute, etc.

The graphics library 116 may include a WebGL or OpenGL mesh compression to reduce a mesh file size, for example. The graphics library 116 may provide the 3D object data model in a form for display on a browser, for example. In some examples, a 3D object data model viewer may be used to display images of the 3D objects data models. The 3D object data model viewer may be implemented using WebGL within a web browser, or OpenGL, for example.

The database 106 may store all data sets for a 3D object data model in any number of various forms from raw data captured to processed data for display. In addition, the database may store one or more statistical models for the 3D object data model.

The output target 108 may include a number of different targets, such as a webpage on the Internet, a search engine, a database, etc. The output target 108 may include a 3D object data model viewer that enables product advertisements or product searches based on the 3D object data model.

In examples herein, the system 100 may be used to acquire data of an object, process the data to generate a 3D object data model, and render the 3D object data model for display. In some instances, an array of lights may be controlled to determine properties of an object.

Figure 2:
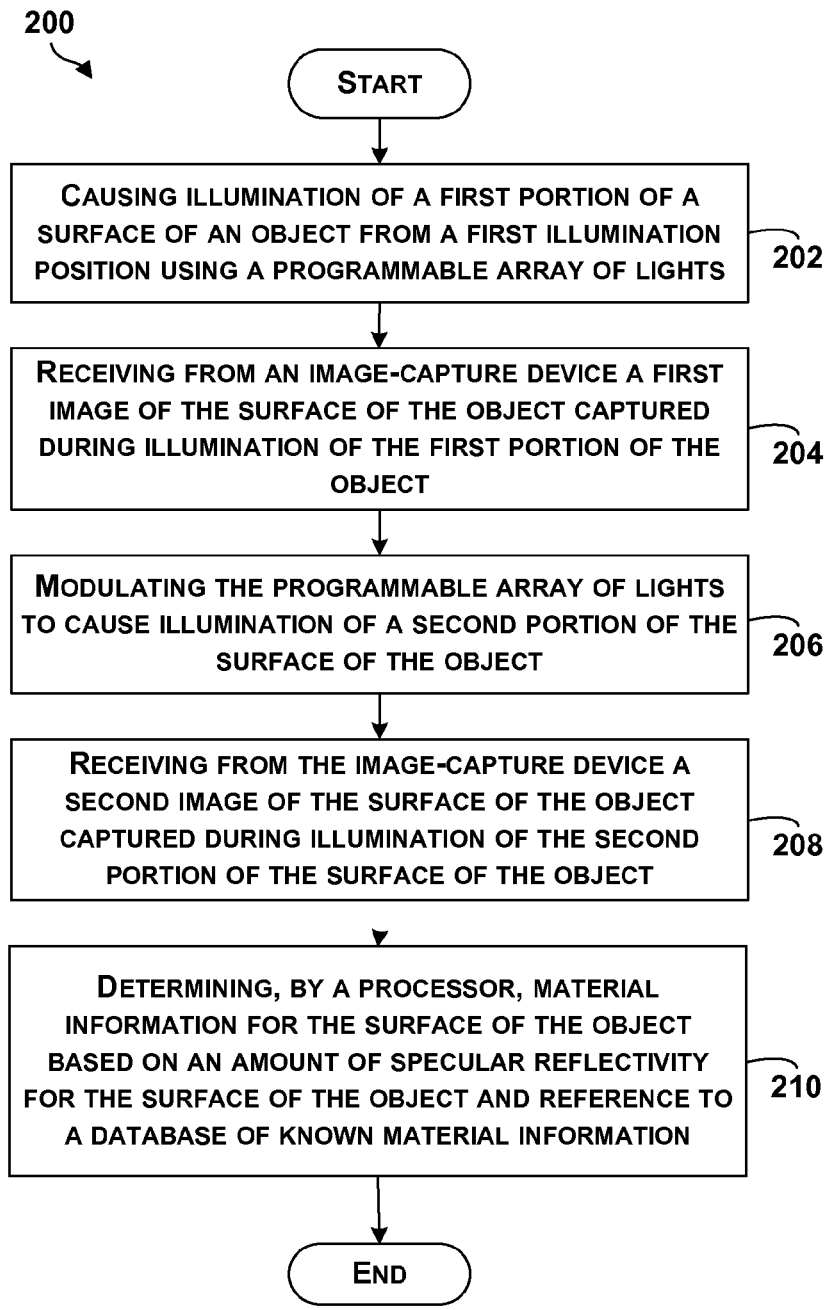
FIG. 2 is a block diagram of an example method for controlling an array of lights to determine properties of an object.

FIG. 2 is a block diagram of an example method 200 for controlling an array of lights to determine properties of an object. Method 200 shown in FIG. 2 presents an embodiment of a method that could be used by the system 100 of FIG. 1 or the system 300 of FIGS. 3A-3B, for example. Method 200 may include one or more operations, functions, or actions as illustrated by one or more of blocks 202-210. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 200 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

In addition, for the method 200 and other processes and methods disclosed herein, each block in FIG. 2 may represent circuitry that is wired to perform the specific logical functions in the process.

Initially, at block 202, the method 200 includes causing illumination of a first portion of a surface of an object from a first illumination position using a programmable array of lights. In one example, modular panels of lights may be combined to form an array of lights. The array of lights may also be controllable such that one or more of the lights or panels of lights may be turned on or off at different instances. This may enable uniquely illuminating a portion of a surface of an object from multiple angles. The type of light may be visible or infrared, among other possibilities.

As an example, multiple modular light-emitting diode (LED) arrays may be coupled to one another and positioned around a pedestal on which the object is placed. The lights may be connected to a controller that may be configured to modulate one or more of brightness, color, number of LEDs illuminated, or other parameters of the arrays to cause illumination of the object from multiple viewpoint positions under various lighting conditions. In some instances, a position and/or orientation of one or more of the arrays may also be adjusted by the controller. For example, one or more actuators may tilt or move a panel of lights.

At block 204, the method 200 includes receiving from an image-capture device a first image of the surface of the object captured during illumination of the first portion of the object. For example, a camera or other type of imaging device may be configured to capture images or video of portions of the surface of the object. The first image may also be of any size and/or resolution and may include color and appearance information for the first portion of the surface of the object.

At block 206, the method 200 includes modulating the programmable array of lights to cause illumination of a second portion of the surface of the object. For example, a controller configured to modulate lights of the array may cause one or more additional lights to be illuminated and/or cause one or more of lights that were previously illuminated to cause illumination of the object from the first illumination position to no longer be illuminated. In some instances, this may cause illumination of the object from a second illumination position that is different than the first illumination position. In another example, the modulation may include a change in illumination color or brightness.

Subsequently color and material information may be received for the second portion of the object. At block 208, the method 200 includes receiving from the image-capture device a second image of the surface of the object captured during illumination of the second portion of the surface of the object. The second image may also include color and appearance information for the second portion of the surface of the object and may be of a same or different size and/or resolution than the first image.

At block 210, the method 200 includes determining, by a processor, material information for the surface of the object based on an amount of specular reflectivity for the surface of the object and reference to a database of known material information. Specular reflection refers to the mirror-like reflection of light from a surface, in which light from a single incoming direction is reflected into a single outgoing direction. Specular reflection is distinct from diffuse reflection which primarily causes the visibility of objects, where incoming light is reflected in a broad range of many angles. While diffuse reflections ordinarily exhibit minor variations in color due to different viewing directions, specular reflections are more dependent on illumination color and position.

In one example, amounts of specular reflectivity may be determined for the first image and the second image using image processing techniques. For example, the difference in behavior between diffuse and specular reflections lends itself to techniques for detecting specular reflections in an image as will be understood by one or ordinary skill in the art. Various approaches for identifying specular reflections use different information such as color in an image, polarization of an illumination source, or images from multiple views of an object.

In some examples, the first portion and the second portion of the surface of the object may include a common portion for which the surface of the object is illuminated from multiple directions. For example, the common portion may be illuminated from the first illumination position in the first image and may be illuminated from the second position in the second image. By determining the color information for given pixels (e.g., in RGB color space) in the images, specular reflections may be determined. As an example, the spectral distribution of a specular reflection may be similar to that of an illumination color, while the spectral distribution of diffuse reflections may be a product of illumination color and surface pigments of the object. Additionally, given information about the illumination color, the color of a given pixel may be viewed as a linear combination of object reflectance color and illumination color.

Other methods for determining amounts of specular reflectivity in the first and second portions are also possible. For example, specular highlights (i.e., bright spots of light that appear on shiny objects when illuminated) may also be identified in the first and/or second image using known image processing methods. One example method utilizes a truncated least squares approximation of a function that maps the color distribution between two images of an object under different illumination conditions to detect specular highlights. The amount or existence of specular highlights, as well as information about changes in specular highlights between the first and second image may also be used determine an amount of specular reflectivity.

In one example, based on the determined amount of specular reflectivity, a database of known amounts of specular reflectivity for different types of materials may be referenced. For example, the database may include materials such as chrome, glass, plastic, rubber, wood, metal, etc. In one instance, the database may have been created by capturing a first and second image of an object of a known material type while illuminated from the first illumination position and the second illumination position and determining the amount of specular reflectivity in the first and second image. This information may then be stored in the database with the type of material for a plurality of types of materials. Given an amount of specular reflectivity for an unknown material type, the database may be referred to classify or categorize the object as a type of material having an amount of specular reflectivity that is closest to the determined amount of specular reflectivity.

In other examples, the first portion of the object and the second portion of the object may include multiple types of materials. Based on an amount of specular reflectivity for the first portion and an amount of specular reflectivity for the second portion, the database may be referred to differentiate between the types of materials. In one instance, the specular reflectivity for the first portion may be used to infer that the first portion is made of a first type of material and the specular reflectivity of the second portion may be used to infer that the second portion is made of a type of material that is different from the first type.

In further examples, multiple images may be captured from same or separate viewpoint positions while the surface of the object is illuminated from the first and/or second illumination positions. For instance, a given image may be captured for a given viewpoint position of the separate viewpoint positions. In some examples, multiple image-capture devices may be used. The image-capture devices may be same or different image-capture devices. For example, a first camera and a second camera may both capture images of the surface of the object during illumination from the first illumination position and the second illumination position. In yet another example, a first image-capture device may be used to capture the first image during the illumination from the first illumination position and a second image-capture device may be used to capture the second image during the illumination from the second illumination position.

Figure 3A:
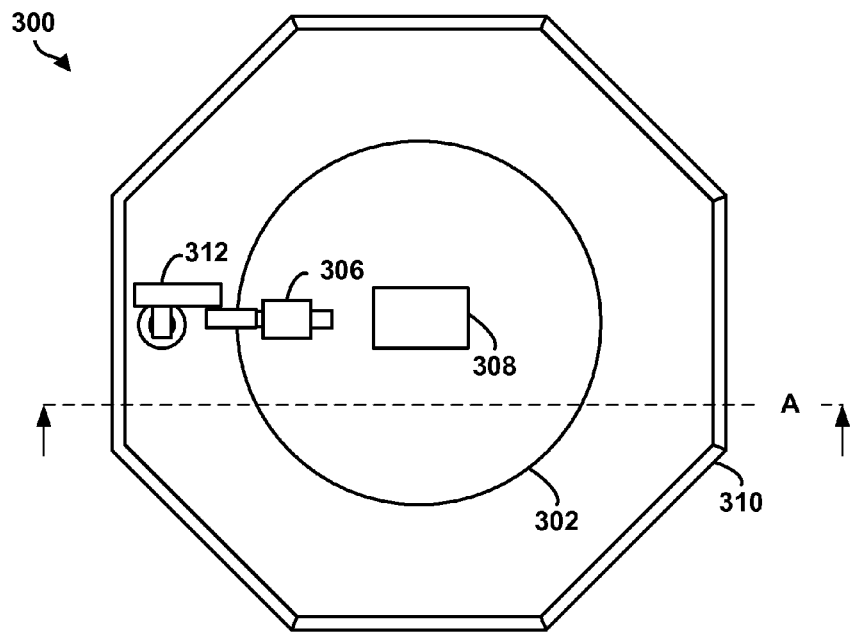
FIG. 3A illustrates a top view of an example system for determining properties of an object.
Figure 3B:
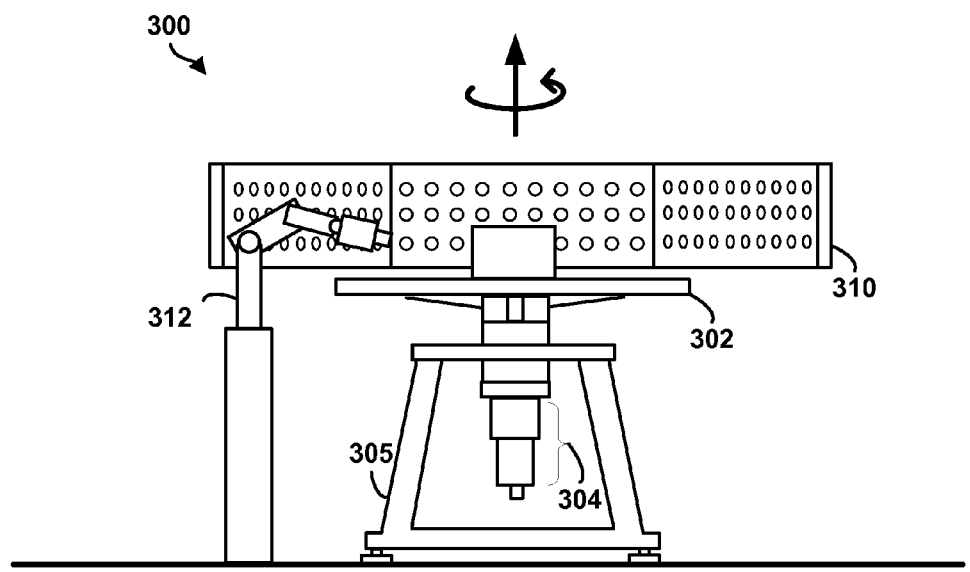
FIG. 3B illustrates a cross-sectional view of the example system for determining properties of an object.

FIG. 3A and FIG. 3B illustrate a top view and cross-sectional view of an example system 300 for controlling an array of lights. The cross-sectional view in FIG. 3B is a view from the intersection of FIG. 3A with the dotted line A. In some examples, the system 300 may include a rotatable surface 302. Although the rotatable surface 302 is illustrated as a circular surface, other shapes are also possible. In one instance, a computing device of the system may be configured to cause the rotatable surface 302 to incrementally or continuously rotate using a drive system 304. The drive system 304, for example, may include one or more motors and motor drive systems configured to receive commands from a computing device and control rotation of the one or more motors. Other drive systems are also possible, and in some instances, the rotatable surface 302 may be configured to be rotated manually (e.g., by an operator of the system 300). The rotatable surface 302 and the drive system 304 may be supported by a support 305.

The system 300 may also include one or more image-capture devices 306, configured to determine information associated with an object 308. The one or more image-capture devices 306 may be 3D scanning devices, cameras, or other types of devices capable of determining 2D or 3D information associated with the object 308 (or surfaces of the object 308) and sending the information to the computing device. The one or more image-capture devices 306 may also be stationary or mobile. The object 308 may be any type of object (e.g., a shoe, purse, computer, statue, or a toy), and may be of any size and number of materials.

In some examples, the one or more image-capture devices 306 may capture information (e.g., an image or a video) during illumination of the object 308. The computing device of the system may cause a programmable light array 310 to illuminate a portion of the object 308 from a given illumination position. For example, the light array 310 is shown as multiple modular arrays of lights that are coupled to one another. However, other configurations including more or less arrays or dissimilar arrays or lighting components are also possible. The computing device may cause illumination of one or more of the lights of the programmable light array 310 to provide illumination of the object from a predetermined illumination position. For instance, causing illumination of a first number of lights of the programmable light array 310 may cause illumination from a first illumination position and causing the number of lights that are illuminated to change may cause illumination from a different position. In one instance, the programmable light array 310 may be caused to iterate through a predetermined sequence of illumination positions.

In some examples, the illumination position may change as the rotatable surface 302 rotates. In other examples, the one or more image-capture devices 306 may also be adjusted while the rotatable surface 302 rotates and/or the illumination position changes. For instance, a positioning component 312 may adjust the position(s) of the one or more image-capture devices 306. As an example, the positioning component 312 may be a positioning component 312 with six degrees of freedom that is capable of rotating, panning, moving, or titling an image-capture device to any position with respect to the object 308. Although the positioning component 312 is shown as a robotic arm, other types of positioning devices or structures may also be used. For instance, the one or more image-capture devices 306 may be attached to a single or multiple-axis motion controller with any number of actuators and rotary or linear servo motors.

In some examples, the programmable light array 310 may enable high dynamic range (HDR) imaging of the object 308. For example, a sequence of images of the object 308 or a portion of the object 308 may be captured while the object 308 is illuminated using a varying amount of intensities. A plurality of images having varying exposure levels may then be processed together to determine an image having a greater dynamic range (i.e., a range between a lightest area and darkest area of the image) as compared to image(s) captured using a single exposure level.

In another example, the system 300 may include another positioning component (not shown) capable of changing the orientation of the object 308. For instance, the another positioning component may be a robotic arm that is configured to lift, rotate, and lower the object 308 to adjust an orientation of the object 308.

In some examples, the presence of predetermined patterns within an image captured using the system 300 may also be used to determine that a surface of an object is reflective or comprises reflective material. For example, a registration pattern that is recognizable in an image, but should not be viewable from a position of an image-capture device, may be identified within an image. The appearance of the registration pattern may indicate that the surface of the object on which the registration pattern appears is reflective. For example, the registration pattern may be an image of the image-capture device or an image of a pattern on the image-capture device.

In one example, the pattern may be a barcode or a quick response (QR) code. In other examples, the pattern may be a pattern a unique pattern printed on the image-capture device (e.g., a pattern above a lens of the image-capture device). Image processing techniques may be used to match the obtained image to a predetermined pattern to determine whether the pattern is within the image. One example image matching method involves matching image descriptors within images. However, various image matching methods as well known to one of ordinary skill in the art may also be used.

In another example, the registration pattern in the image may be caused by a secondary signal. For instance, the secondary signal may be a laser that is reflecting off a mirror or other type of reflective surface of the object and appearing on a wall or other surface that is adjacent to the object and/or not part of the object. For example, a second image-capture device may capture images of a wall while the laser signal is directed at the object and the obtained images may be processed to determine whether the laser signal is present. In one instance, a first camera may be at 0 degrees (with respect to the perimeter of the rotatable surface 302) and may obtain an image of a surface of the object. Also, a laser may be positioned at 45 degrees and a partition or rectangular surface may be curved around the perimeter of the rotatable surface 302 from 270 to 360 degrees. A second camera may be configured to capture an image of a portion of the partition on which a laser signal directed at the surface of the object would appear if the surface of the object facing the first camera were reflective.

Figure 4A:
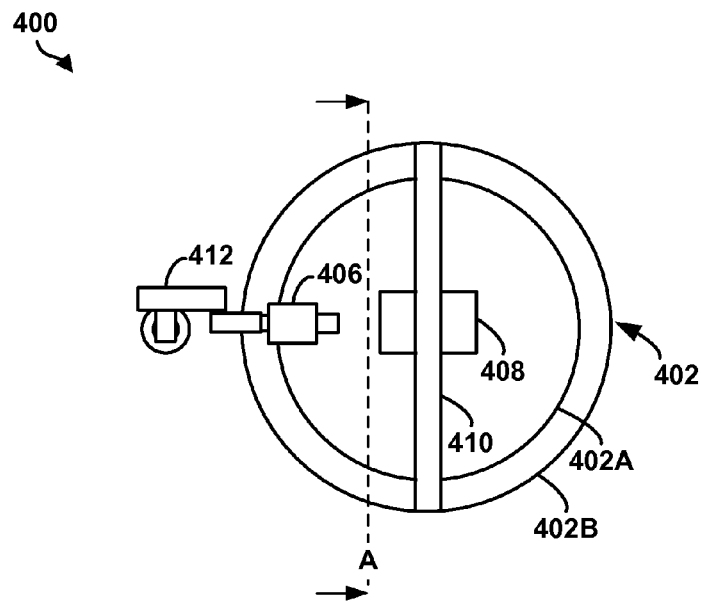
FIG. 4A illustrates a top view of another example system for determining properties of an object.
Figure 4B:
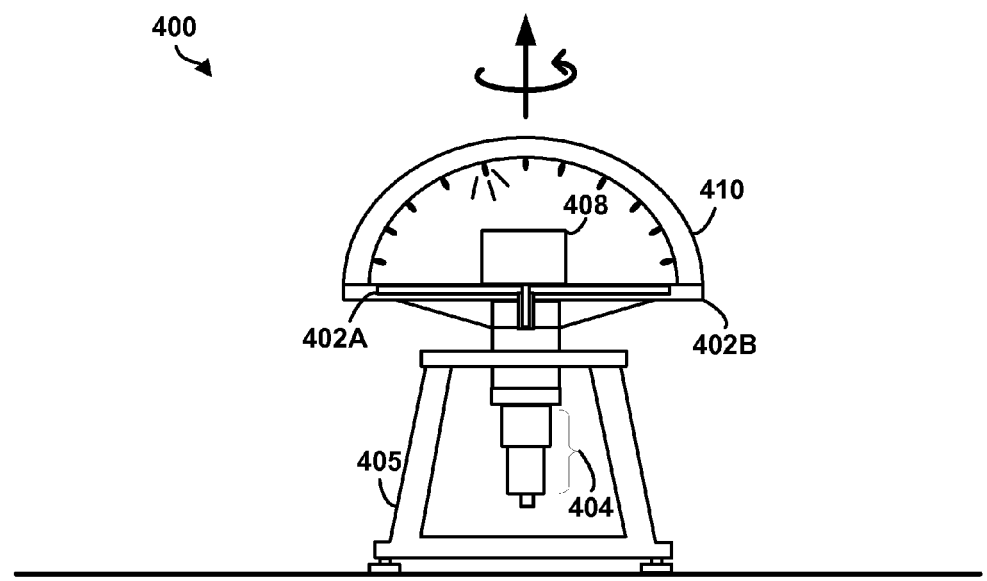
FIG. 4B illustrates a cross-sectional view of the another example system for determining properties of an object.

Different configurations including different components or more or less components than the system 300 are also possible. FIG. 4A and FIG. 4B illustrate a top view and cross-sectional view of another example system 400 for controlling an array of lights. The cross-sectional view in FIG. 4B is a view from the intersection of FIG. 4A with the dotted line A. Similar to the system 300 of FIGS. 3A and 3B, the system 400 may include a rotatable surface 402, a drive system 404, a support 405, as well as one or more image-capture devices 406 configured to obtain information associated with an object 408. The rotatable surface may include an inner rotatable surface 402A, and an outer rotatable surface 402B that may each be rotated by the drive system 404 or by an operator. The inner rotatable surface 402A and the outer rotatable surface 402B may also be configured to be rotated jointly or independently. In some examples, a programmable array of lights 410 may be coupled to the outer rotatable surface 402B. For instance, the programmable array of lights 410 may be a strip of lights (e.g., LEDs) that form an arch above the rotatable surface 402. The programmable array of lights 410 may include one or more lights positioned along the arch. In addition, the system 400 may include a positioning component 412 capable to pan, tilt, or move an image-capture device with respect to the object 408.

In one example, the system 400 may be used to determine bidirectional reflectance distribution function (BRDF) samples for the object 408. For example, a BRDF for an object may define how light is reflected at a surface of the object 408, as well known to one of ordinary skill in the art. The BRDF may be a four-dimensional function which takes an incoming light direction and an outgoing direction, both defined with respect to a surface normal, and returns the ratio of the reflected radiance exiting along the outgoing direction to the irradiance incident on the surface from the incoming direction. In some examples, the incoming direction may be the direction from an illumination position to the object and the outgoing direction may be the direction from the object to a viewpoint position from which an image-capture device captures an image. In one example, the surface normal of the object may be determined based on a 3D point cloud received from a 3D scanner.

By causing the programmable array of lights 410 to illuminate lights of the array in a sequence (e.g., blink a first light, blink a second light, blink a third light, or blink a group of adjacent lights, blink a next group of adjacent lights), reflectance ratios may be determined for hemispherical strips in the BRDF function space. For instance, an amount of reflected radiance may be determined based on an image of the surface of the object. In some examples, a brightness or saturation of portions of the image may be used to determine an amount of reflected radiance. In a further example, the one or more image-capture devices 406 may include a high-speed camera. Images from the high-speed camera obtained during a sequential illumination of the programmable array of lights 410 may be processed to determine relative amounts of reflected radiance for each of the illumination positions of the sequence.

Additionally, in some instances, the programmable array of lights 410 and/or the object 408 may be rotated to determine reflectance ratios for another strip of the BRDF function space. In some instances, the position(s) of the one or more image-capture devices 406 may also be adjusted to determine additional BRDF samples. Thus, the system 400 may be used to obtain information for strips in the BRDF function space.

In some examples, based on a difference between a first reflectance ratio while the object 408 is illuminated from a first illumination position of the programmable array of lights 410 and a second reflectance ratio determined while the surface of the object 408 is illuminated from a second illumination position, material information for the object 408 may be determined. For instance, a database of known bidirectional reflectance distribution functions for a plurality of types of materials may be referenced to determine surface properties of a portion of the object 408. Given one or more reflectance ratios that are defined with respect to an incoming direction and an outgoing direction, a type of material having a BRDF with reflectance ratios that closest match the one or more reflectance ratios may be determined. Thus, in some examples, the object 408 or portions of the object 408 may be classified or categorized as a known type(s) of material based on BRDF samples obtained using the system 400.

Different configurations including different components or more or less components than the system 400 are also possible. As one example, the system in FIGS. 3A-B or 4 may be configured to have a light-array housing that encloses an object, such that a light array may be positioned at all angles surrounding an object or at any angle surrounding an object.

Figure 5:
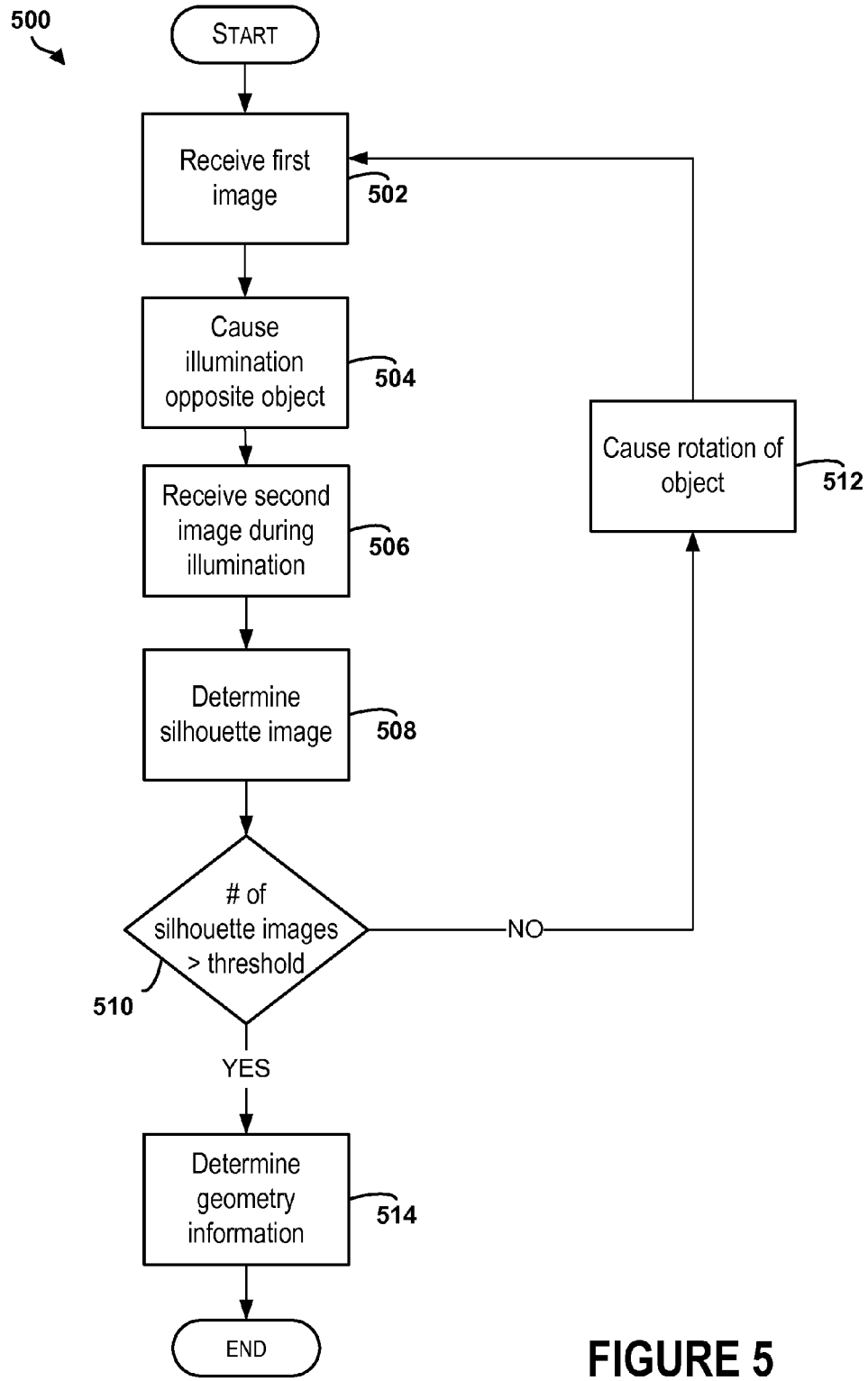
FIG. 5 is an example flow chart for determining geometric information associated with an object.

In some instances, the system 300 of FIGS. 3A-3B may be used to determine geometric properties of an object. FIG. 5 is an example flow chart 500 for determining geometric information associated with an object. As shown in FIG. 5, at block 502, a first image of an object may be received. For example, the image may be captured during little or no illumination. In one instance, the image may be captured while the object is illuminated from a direction that is above the object.

At step 504, a processor of a computing device may cause illumination of the object from a direction that is opposite to a direction from which an image-capture device obtains an image. In one example, the object may be positioned between an illumination position and an image-capture device such that a light source illuminates a side of the object that is not exposed to the image-capture device. In one instance, with reference to positions around the rotatable surface 302 of FIGS. 3A-3B, an image-capture device may be at 0 degrees while the illumination position is at 180 degrees.

At block 506, a second image is received during the illumination opposite the object. In one instance, the image-capture device may be a high-speed camera that captures an image before the illumination and during the illumination. In other examples, the first and second image may be frames of a high-definition video. It is contemplated that the first image or the second image may encompass groups of multiple images or frames of a video, or an image that is determined by combining information from a group of images as well.

In one instance, based on changes in the first image and second image, at block 508, a silhouette image may be determined. For example, in the second image, portions of the image that include changes in brightness or saturation with respect to the first image due to the illumination of the object may be determined to be outside the shape of the object. Also, portions of the image that do not change with respect to the first image, because the illumination does not illuminate the surface of the object that is exposed to the image-capture device, may be used to determine an outline of the shape of the object. By determining where portions of the image change during the illumination opposite the position of the high speed camera, the silhouette of the object may be extracted from the image.

At block 510, a determination may be made whether a predetermined number of silhouette images has been determined. For example, the number may be 4, and if the number is less than 4, at block 512, a computing device may cause rotating of the object. In one example, the rotatable surface 302 may rotate the object by an incremental amount (such as 20 degrees, 45 degrees, 90 degrees, etc.). Subsequently, blocks 502-508 may be repeated to determine another silhouette image for another side of the image.

In some examples, if the number of silhouette images is greater than the threshold, geometry information may be determined for the object at block 514. For instance, if the number of silhouette images is four and the image is caused to be rotated by 45 degrees at block 512, four silhouette images from a front, left side, back, and right side of an object may be determined. The images may subsequently be processed and merged to form an approximate visual hull that is consistent with the four silhouettes of the object. For example, shape-from-silhouette 3D reconstruction techniques or other image-based visual hull approximation techniques from silhouettes may be used, as well known to one of ordinary skill in the art. Thus, silhouette images from multiple sides of an object may be combined to determine a geometric model of the object.

In another example configuration, illumination may be caused from a position that is adjacent to an image-capture device, and a shadow of the object may be projected onto a background. The background may be visible to the image-capture device. For instance, the object may be at the center of the rotatable surface 302 of FIGS. 3A-3B, the illumination position may be at 90 degrees (with reference to the perimeter of the rotatable surface 302) and project a shadow onto a known background at 270 degrees. The image-capture device may be at 0 degrees and may be able to capture an image of the background before, during, and after the illumination. Brightness or intensity of portions of the image of the background that are outside the shape of the object may change as the intensity of the illumination changes, while portions within the shadow of the object may be affected less by the illumination. By isolating portions of the image that are shadows, an outline or silhouette of the object may be determined.

Figure 6:
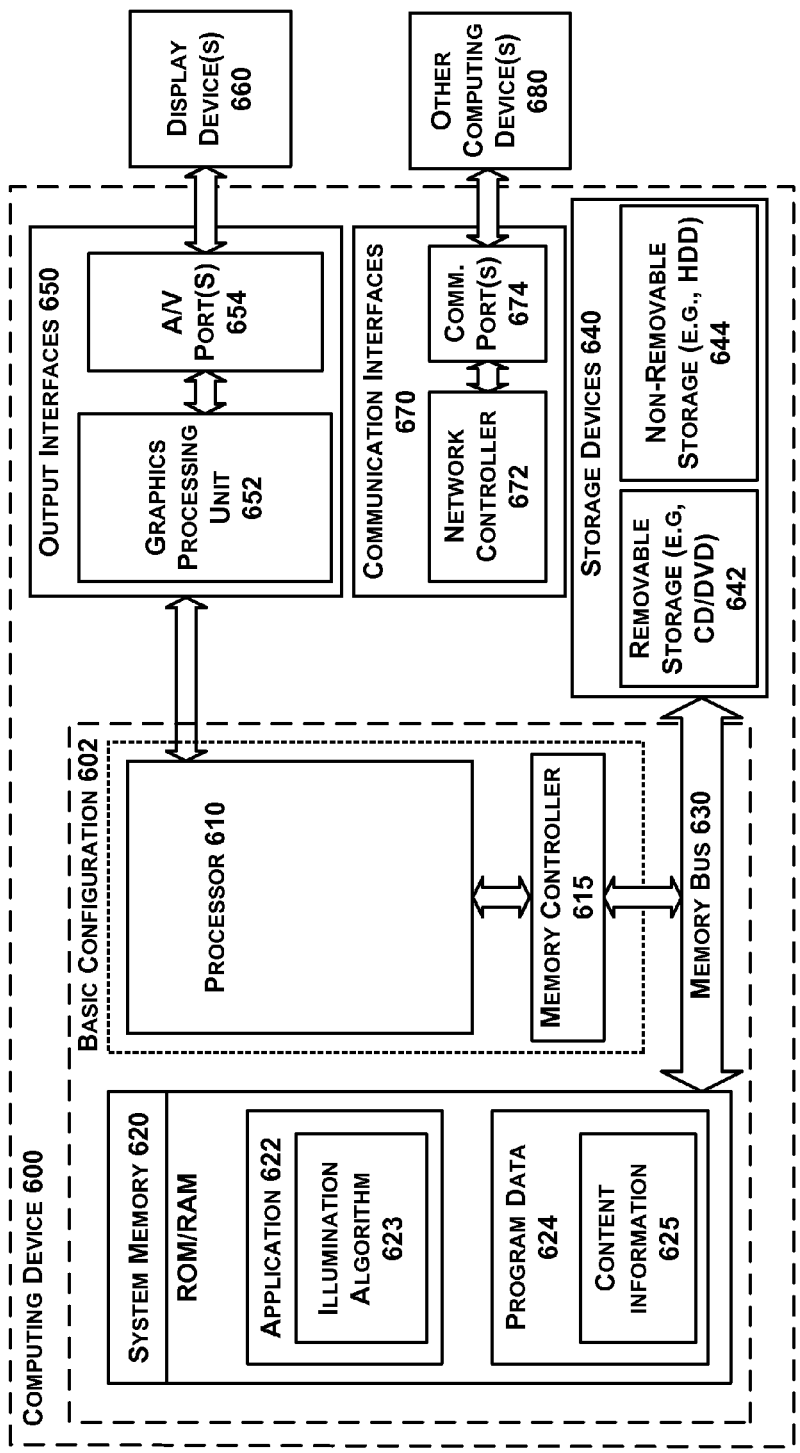
FIG. 6 is a functional block diagram illustrating an example computing device used in a computing system that is arranged in accordance with at least some embodiments described herein.

FIG. 6 is a functional block diagram illustrating an example computing device 600 used in a computing system that is arranged in accordance with at least some embodiments described herein. The computing device 600 may be a personal computer, mobile device, cellular phone, touch-sensitive wristwatch, tablet computer, video game system, or global positioning system, and may be implemented to provide a system for multi-modal three-dimensional (3D) scanning of objects as described in FIGS. 1-5. In a basic configuration 602, computing device 600 may typically include one or more processors 610 and system memory 620. A memory bus 630 can be used for communicating between the processor 610 and the system memory 620. Depending on the desired configuration, processor 610 can be of any type including but not limited to a microprocessor (μP), a microcontroller (μC), a digital signal processor (DSP), or any combination thereof. A memory controller 615 can also be used with the processor 610, or in some implementations, the memory controller 615 can be an internal part of the processor 610.

Depending on the desired configuration, the system memory 620 can be of any type including but not limited to volatile memory (such as RAM), non-volatile memory (such as ROM, flash memory, etc.) or any combination thereof. System memory 620 may include one or more applications 622, and program data 624. Application 622 may include an illumination algorithm 623 that is arranged to provide inputs to the electronic circuits, in accordance with the present disclosure. Program data 624 may include content information 625 that could be directed to any number of types of data. In some example embodiments, application 622 can be arranged to operate with program data 624 on an operating system.

Computing device 600 can have additional features or functionality, and additional interfaces to facilitate communications between the basic configuration 602 and any devices and interfaces. For example, data storage devices 640 can be provided including removable storage devices 642, non-removable storage devices 644, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Computer storage media can include volatile and nonvolatile, non-transitory, removable and non-removable media implemented in any method or technology for storage of information, such as computer readable instructions, data structures, program modules, or other data.

System memory 620 and storage devices 640 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media can be part of computing device 600.

Computing device 600 may also include output interfaces 650 that may include a graphics processing unit 652, which can be configured to communicate to various external devices such as display devices 660 or speakers via one or more A/V ports or a communication interface 660. The communication interface 670 may include a network controller 672, which can be arranged to facilitate communications with one or more other computing devices 680 over a network communication via one or more communication ports 674. The communication connection is one example of a communication media. Communication media may be embodied by computer readable instructions, data structures, program modules, or other data in a modulated data signal, such as a carrier wave or other transport mechanism, and includes any information delivery media. A modulated data signal can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media.

Computing device 600 can be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 can also be implemented as a personal computer including laptop computers, tablet computers, netbooks computers, and other computer configurations.

Figure 7:
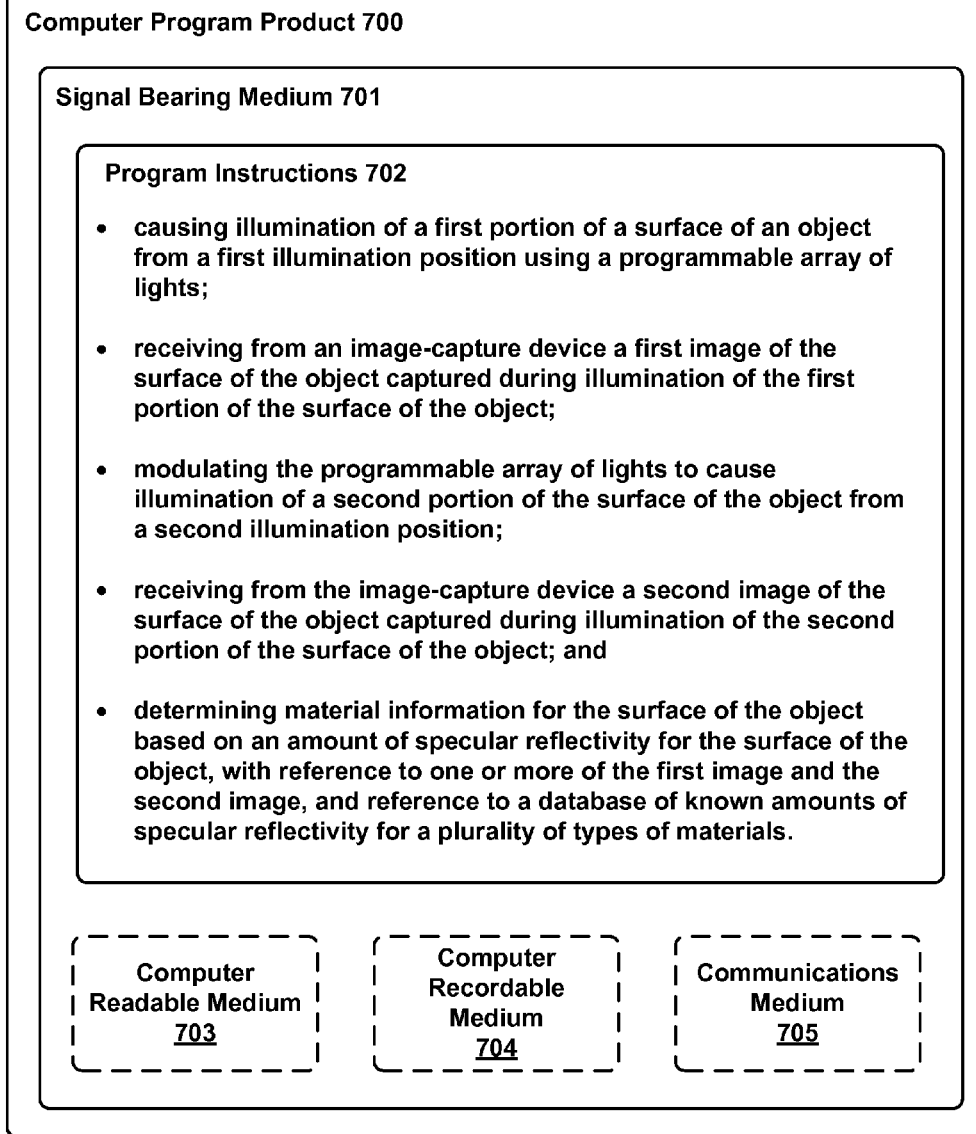
FIG. 7 is a schematic illustrating a conceptual partial view of an example computer program product that includes a computer program for executing a computer process on a computing device, arranged according to at least some embodiments presented herein.

In some embodiments, the disclosed methods may be implemented as computer program instructions encoded on a non-transitory computer-readable storage media in a machine-readable format, or on other non-transitory media or articles of manufacture. FIG. 7 is a schematic illustrating a conceptual partial view of an example computer program product 700 that includes a computer program for executing a computer process on a computing device, arranged according to at least some embodiments presented herein.

In one embodiment, the example computer program product 700 is provided using a signal bearing medium 701. The signal bearing medium 701 may include one or more programming instructions 702 that, when executed by one or more processors may provide functionality or portions of the functionality described above with respect to FIGS. 1-6. In some examples, the signal bearing medium 701 may encompass a computer-readable medium 703, such as, but not limited to, a hard disk drive, a Compact Disc (CD), a Digital Video Disk (DVD), a digital tape, memory, etc. In some implementations, the signal bearing medium 701 may encompass a computer recordable medium 704, such as, but not limited to, memory, read/write (R/W) CDs, R/W DVDs, etc. In some implementations, the signal bearing medium 701 may encompass a communications medium 705, such as, but not limited to, a digital and/or an analog communication medium (e.g., a fiber optic cable, a waveguide, a wired communications link, a wireless communication link, etc.). Thus, for example, the signal bearing medium 701 may be conveyed by a wireless form of the communications medium 705 (e.g., a wireless communications medium conforming with the IEEE 802.11 standard or other transmission protocol).

The one or more programming instructions 702 may be, for example, computer executable and/or logic implemented instructions. In some examples, a computing device such as the computing device 600 of FIG. 6 may be configured to provide various operations, functions, or actions in response to the programming instructions 702 conveyed to the computing device 600 by one or more of the computer readable medium 703, the computer recordable medium 704, and/or the communications medium 705.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
   causing illumination of a first portion of a surface of an object from a first illumination position using a programmable array of lights;
   receiving from at least one camera a first image of the surface of the object captured during illumination of the first portion of the surface of the object;
   modulating the programmable array of lights to cause illumination of a second portion of the surface of the object from a second illumination position;
   receiving from the at least one camera a second image of the surface of the object captured during illumination of the second portion of the surface of the object; and
   determining, by a processor, material information for the surface of the object based on an amount of specular reflectivity for the surface of the object, with reference to one or more of the first image and the second image, and reference to a database of known amounts of specular reflectivity for a plurality of types of materials.

2. The method of claim 1, further comprising:
   determining the first portion of the surface of the object includes a first material and determining the second portion of the surface of the object includes a second material that is different from the first material.

3. The method of claim 1, further comprising:
   receiving multiple images of the surface of the object from separate viewpoint positions while the surface of the object is illuminated from the first illumination position and the second illumination position, wherein a given image is captured from a given viewpoint position of the separate viewpoint positions.

4. The method of claim 3, wherein receiving from at least one camera a first image of the surface of the object captured during illumination of the first portion of the surface of the object comprises receiving an image of the surface of the object from a first viewpoint position from a first camera and receiving another image of the surface of the object from a second viewpoint position from a second camera.

5. The method of claim 3, further comprising:
   causing rotation of the object such that the multiple images of the surface of the object are obtained from the separate viewpoint positions.

6. The method of claim 1, further comprising:
   determining a first reflectance ratio while the surface of the object is illuminated from the first illumination position, wherein a reflectance ratio is a ratio between an amount of radiance reflected in a direction of a viewpoint position and an amount of irradiance incident on the surface of the object from an illumination position;
   determining a second reflectance ratio while the surface of the object is illuminated from the second illumination position; and
   determining material information for the object based on a comparison of the first reflectance ratio and the second reflectance ratio and a corresponding comparison of the first illumination position and the second illumination position.

7. The method of claim 6, further comprising:
   receiving multiple images of the surface of the object from separate viewpoint positions while the surface of the object is illuminated from the first illumination position and the second illumination position, wherein a given image is captured from a given position of the separate positions; and
   determining multiple reflectance ratios based on directions to the separate viewpoint positions and directions to the first illumination position and the second illumination position; and
   determining material information for the surface of the object based on the multiple reflectance ratios and a database of known bidirectional reflectance distribution functions for a plurality of types of materials.

8. The method of claim 1, further comprising:
   determining a first silhouette of the object based on one or more images captured while the object is positioned between the first illumination position and the at least one camera;
   causing rotation of the object such that another surface of the object is exposed to the at least one camera;
   determining a second silhouette of the object based on one or more images captured while the another surface of the object is exposed and the object is positioned between the first illumination position and the at least one camera; and
   determining geometry information for the object based on the first silhouette and the second silhouette.

9. The method of claim 1, further comprising:
   recognizing a registration pattern in the first image; and
   determining a portion of the surface of the object is reflective based on the presence of the registration pattern.

10. The method of claim 9, wherein the registration pattern includes an image of the at least one camera.

11. The method of claim 9, wherein the registration pattern includes a laser signal that is reflected by the portion of the surface of the object onto a surface that is adjacent to the object.

12. A non-transitory computer-readable medium having stored therein instructions executable by a computing device having at least one processor to cause the computing device to perform functions comprising:
   causing illumination of a first portion of a surface of an object from a first illumination position using a programmable array of lights;
   receiving from at least one camera a first image of the surface of the object captured during illumination of the first portion of the surface of the object;
   modulating the programmable array of lights to cause illumination of a second portion of the surface of the object from a second illumination position;
   receiving from the at least one camera a second image of the surface of the object captured during illumination of the second portion of the surface of the object; and
   determining material information for the surface of the object based on an amount of specular reflectivity for the surface of the object, with reference to one or more of the first image and the second image, and reference to a database of known amounts of specular reflectivity for a plurality of types of materials.

13. The non-transitory computer readable medium of claim 12, further comprising instructions executable by the computing device to cause the computing device to perform functions comprising receiving from a first camera an image of the surface of the object captured from a first viewpoint position and receiving from a second camera another image of the surface of the object captured from a second viewpoint position.

14. The non-transitory computer readable medium of claim 12, further comprising instructions executable by the computing device to cause the computing device to perform functions comprising:

determining a first reflectance ratio while the surface of the object is illuminated from the first illumination position, wherein a reflectance ratio is a ratio between an amount of radiance reflected in a direction of a viewpoint position and an amount of irradiance incident on the surface of the object from an illumination position;

determining a second reflectance ratio while the surface of the object is illuminated from the second illumination position; and determining material information for the object based on a difference between the first reflectance ratio and the second reflectance ratio and a corresponding difference between the first illumination position and the second illumination position.

15. The non-transitory computer readable medium of claim 12, further comprising instructions executable by the computing device to cause the computing device to perform functions comprising:

determining a first silhouette of the object based on one or more images captured while the object is positioned between the first illumination position and the at least one camera;

causing rotation of the object such that another surface of the object is exposed to the at least one camera;

determining a second silhouette of the object based on one or more images captured while the another surface of the object is exposed and the object is positioned between the first illumination position and the at least one camera; and determining geometry information for the object based on the first silhouette and the second silhouette.

16. The non-transitory computer readable medium of claim 12, further comprising instructions executable by the computing device to cause the computing device to perform functions comprising:

recognizing a registration pattern in the first image; and determining a portion of the surface of the object is reflective based on the presence of the registration pattern.

17. A system comprising:

a light array configurable to illuminate a surface of an object from multiple illumination positions;

one or more cameras configured to obtain images of the object while the surface of the object is illuminated;

a database of known material information for a plurality of types of materials; and a processor configured to:
   determine an amount of specular reflectivity for a portion of the surface of the object based on the obtained images; and
   determine material information for the surface of the object based on the amount of specular reflectivity and reference to the database of known material information.

18. The system of claim 17, further comprising:

one or more control arms configured to adjust a position of the light array or the one or more cameras based on instructions from the processor.

19. The system of claim 18, wherein the light array includes a linear array of lights configured to be modulated while the one or more control arms adjust the position of the one or more cameras.

20. The system of claim 17, further comprising:

a rotation component comprising a rotatable surface and a drive system, wherein the rotation component is configured to rotate the object such that multiple images of the surface of the object are obtained from separate viewpoint positions.

* * * * *